(12) United States Patent
Merrifield et al.

(10) Patent No.: US 10,147,146 B2
(45) Date of Patent: Dec. 4, 2018

(54) TAILORING SOCIAL ELEMENTS OF VIRTUAL ENVIRONMENTS

(75) Inventors: Lane Merrifield, Kelowna (CA); Lancelot Darren Priebe, Kelowna (CA)

(73) Assignee: Disney Enterprises, Inc., Burbank, CA (US)

(*) Notice: Subject to any disclaimer, the term of this patent is extended or adjusted under 35 U.S.C. 154(b) by 169 days.

(21) Appl. No.: 13/420,397

(22) Filed: Mar. 14, 2012

(65) Prior Publication Data

US 2013/0246942 A1    Sep. 19, 2013

(51) Int. Cl.

| | |
|---|---|
| G06F 3/048 | (2013.01) |
| G06Q 50/00 | (2012.01) |
| A61B 5/11 | (2006.01) |
| A61B 5/16 | (2006.01) |
| A63F 13/67 | (2014.01) |
| A63F 13/798 | (2014.01) |
| G06T 13/40 | (2011.01) |
| G06F 11/34 | (2006.01) |
| G06F 3/0481 | (2013.01) |
| H04L 29/06 | (2006.01) |
| A63F 13/212 | (2014.01) |
| A63F 13/211 | (2014.01) |
| G06F 11/30 | (2006.01) |

(52) U.S. Cl.
CPC .......... *G06Q 50/01* (2013.01); *A61B 5/1118* (2013.01); *A61B 5/1124* (2013.01); *A61B 5/16* (2013.01); *A63F 13/67* (2014.09); *A63F 13/798* (2014.09); *G06F 3/04815* (2013.01); *G06F 11/3409* (2013.01); *G06F 11/3438* (2013.01); *G06T 13/40* (2013.01); *H04L 29/06034* (2013.01); *H04L 29/06401* (2013.01); *H04L 67/38* (2013.01); *A63F 13/211* (2014.09); *A63F 13/212* (2014.09); *A63F 2250/10* (2013.01); *A63F 2250/26* (2013.01); *G06F 11/30* (2013.01); *G06F 11/34* (2013.01)

(58) Field of Classification Search
CPC ....... A61B 5/16; A61B 5/1118; A61B 5/1124; A63F 13/212; A63F 13/211; A63F 13/67; A63F 2250/10; A63F 2250/26; A63F 13/798; G06T 13/40; G06F 3/04815; G06F 11/30; G06F 11/34; G06F 11/3409; G06F 11/3438; H04L 29/06034; H04L 29/06401; H04L 67/38; G06Q 50/01
USPC ................................ 715/757, 850; 345/473
See application file for complete search history.

(56) References Cited

U.S. PATENT DOCUMENTS

| | | | | |
|---|---|---|---|---|
| 5,813,863 | A * | 9/1998 | Sloane ................... | G09B 5/065 434/236 |
| 5,815,147 | A * | 9/1998 | Bogen ................... | A63F 13/005 715/835 |
| 6,219,045 | B1 * | 4/2001 | Leahy .................... | H04W 4/029 715/757 |
| 6,329,986 | B1 * | 12/2001 | Cheng .................... | G06F 3/011 345/419 |

(Continued)

*Primary Examiner* — Ajay M Bhatia
*Assistant Examiner* — Jennifer E Nichols
(74) *Attorney, Agent, or Firm* — Patterson + Sheridan, LLP (57) ABSTRACT

Techniques are disclosed for providing a social platform for a user. In one embodiment, activity of the user is monitored in a virtual environment. A profile is generated for the user, based on the monitored activity. A social element of the virtual environment is modified for the user, based on the generated profile.

17 Claims, 6 Drawing Sheets

(56) References Cited

U.S. PATENT DOCUMENTS

| | | | | |
|---|---|---|---|---|
| 6,396,509 B1* | 5/2002 | Cheng | G06F 3/011 | 715/706 |
| 6,425,764 B1* | 7/2002 | Lamson | A61M 21/00 | 434/236 |
| 6,511,442 B1* | 1/2003 | Lathan | A61B 5/16 | 600/595 |
| 6,517,351 B2* | 2/2003 | Spector | G09B 17/006 | 434/169 |
| 8,026,918 B1* | 9/2011 | Murphy | G06N 3/006 | 345/473 |
| 8,037,416 B2* | 10/2011 | Bates | G06F 3/04815 | 715/745 |
| 8,285,790 B2* | 10/2012 | Bhogal | A63F 13/12 | 709/205 |
| 8,458,602 B2* | 6/2013 | Borst | A63F 13/12 | 715/733 |
| 8,615,479 B2* | 12/2013 | Jung | A61B 5/04842 | 706/46 |
| 2002/0113809 A1* | 8/2002 | Akazawa | G06F 3/04815 | 715/706 |
| 2004/0168117 A1* | 8/2004 | Renaud | G06F 3/016 | 715/201 |
| 2004/0197750 A1* | 10/2004 | Donaher | G09B 7/00 | 434/236 |
| 2005/0216243 A1* | 9/2005 | Graham | G16H 50/50 | 703/11 |
| 2007/0046678 A1* | 3/2007 | Peterson | G09B 5/00 | 345/473 |
| 2007/0066403 A1* | 3/2007 | Conkwright | A63F 13/10 | 463/43 |
| 2008/0195956 A1* | 8/2008 | Baron | G06Q 10/10 | 715/753 |
| 2009/0089157 A1* | 4/2009 | Narayanan | A63F 13/12 | 705/14.23 |
| 2009/0113314 A1* | 4/2009 | Dawson | G06F 3/011 | 715/757 |
| 2009/0113319 A1* | 4/2009 | Dawson | G06F 17/30702 | 715/762 |
| 2009/0158170 A1* | 6/2009 | Narayanan | H04L 67/306 | 715/753 |
| 2009/0259946 A1* | 10/2009 | Dawson | G06Q 30/02 | 715/747 |
| 2009/0288002 A1* | 11/2009 | Hamilton, II | G06F 3/0481 | 715/706 |
| 2009/0299960 A1* | 12/2009 | Lineberger | A63F 13/12 | |
| 2010/0070884 A1* | 3/2010 | Bromenshenkel | G06F 3/0481 | 715/757 |
| 2010/0088600 A1* | 4/2010 | Hamilton, II | A63F 13/12 | 715/706 |
| 2010/0153868 A1* | 6/2010 | Allen | G06T 13/40 | 715/764 |
| 2010/0156909 A1* | 6/2010 | Banerjee | A63F 13/12 | 345/469.1 |
| 2010/0185640 A1* | 7/2010 | Dettinger | G06Q 10/10 | 707/758 |
| 2010/0185721 A1* | 7/2010 | Merrifield | G06Q 10/10 | 709/203 |
| 2010/0203968 A1* | 8/2010 | Gill | G06T 13/40 | 463/32 |
| 2010/0332997 A1* | 12/2010 | Hamilton, II | G06F 21/6218 | 715/757 |
| 2011/0055728 A1* | 3/2011 | Dawson | G06F 3/04815 | 715/753 |
| 2011/0145050 A1* | 6/2011 | Gross | G06Q 10/10 | 705/14.25 |
| 2011/0145591 A1* | 6/2011 | Grzybowski | G06F 9/4451 | 713/189 |
| 2011/0281639 A1* | 11/2011 | Porat | A63F 13/798 | 463/23 |
| 2012/0079121 A1* | 3/2012 | Rapo | H04L 67/38 | 709/227 |
| 2012/0083668 A1* | 4/2012 | Pradeep | A61B 5/04015 | 600/300 |
| 2012/0089598 A1* | 4/2012 | Oztekin | G06F 17/30867 | 707/723 |
| 2012/0135804 A1* | 5/2012 | Bender | A61B 5/165 | 463/36 |
| 2012/0188277 A1* | 7/2012 | Hebbar | A63F 13/52 | 345/629 |
| 2012/0194515 A1* | 8/2012 | Dawson | G06Q 30/02 | 345/419 |
| 2014/0228649 A1* | 8/2014 | Rayner | A61B 5/1118 | 600/301 |

* cited by examiner

TAILORING SOCIAL ELEMENTS OF VIRTUAL ENVIRONMENTS

BACKGROUND

Field

Embodiments presented in this disclosure generally relate to virtual environments and, more particularly, to providing a social platform in a virtual environment.

Description of the Related Art

A virtual world is a simulated environment in which users may interact with virtual objects and locations of the virtual world. Each user may control a respective avatar through which the user may interact with other users' avatars in the virtual world. An avatar generally provides a graphical representation of an individual within the virtual world environment. Avatars are usually presented to other users as two or three-dimensional graphical representations that resembles a human individual. Frequently, virtual worlds allow multiple users to enter the virtual environment and interact with one another. Virtual worlds are said to provide an immersive environment, as they typically appear similar to the real world and objects tend to follow rules related to gravity, topography, locomotion, physics and kinematics. Of course, virtual worlds can suspend or alter these rules as well as provide other imaginative or fanciful environments. Users typically communicate with one another through their avatars using text messages sent between avatars, real-time voice communication, gestures displayed by avatars, symbols visible in the virtual world, and the like.

Some virtual worlds are described as being persistent. A persistent world provides an immersive environment (e.g., a fantasy setting used as a setting for a role-playing game, or a virtual world complete with land, buildings, towns, and economies) that is generally always available and where events continue to occur regardless of the presence of a given avatar. Thus, unlike more conventional online games or multi-user environments, the virtual world continues to exist and plots and events continue to unfold as users enter (and exit) the virtual world. Virtual environments are presented as images on a display screen and some virtual environment may allow users to record events that occur within the virtual environment.

Many virtual worlds feature some form of content filtering for use in detecting and removing offensive content. For example, a virtual world may include a chat filter configured to detect offensive words in communications within the virtual world and to remove them and/or mask the words. In certain virtual worlds, users are given the ability to ignore or block interactions with particular other users in the virtual world. For example, a first user of the virtual world may choose to block interactions with a second user (e.g., because to offensive comments previously made by the second user). Upon blocking interactions with a particular user in the virtual world, the first user may no longer see communications from the second user and in some cases may no longer see the avatar associated with the second user within the virtual world.

SUMMARY

Embodiments of the invention provide a method, computer-readable storage medium and system for performing an operation that includes monitoring activity of a user in one or more virtual environments. The operation also includes generating a profile of the user, based on the monitored activity, where the profile comprises at least one of an activity profile, a developmental profile, and a geographical profile. The operation also includes, based on the generated profile, modifying, for the user, a social element of at least a first one of the virtual environments, where the social element is specific to the user.

BRIEF DESCRIPTION OF THE DRAWINGS

So that the manner in which the above recited aspects are attained and can be understood in detail, a more particular description of embodiments of the invention, briefly summarized above, may be had by reference to the appended drawings.

It is to be noted, however, that the appended drawings illustrate only typical embodiments of this invention and are therefore not to be considered limiting of its scope, for the invention may admit to other equally effective embodiments.

DETAILED DESCRIPTION

Embodiments of the invention provide techniques for providing a social platform in a virtual environment. In one embodiment, social elements of the virtual environment are programmatically tailored for a user, based on an inferred profile of the user. The profile of a user may be generated by monitoring and analyzing activity of the user in the virtual environment. Further, several types of profiles may be inferred, such as activity profiles and developmental profiles. An activity profile specifies activities in the virtual environment that the user often engages in. The activities may be identified based on predetermined criteria, such as based on a relative frequency with which the user engages in the activities. A developmental profile specifies a level of development of the user in the physical world. For example, the level of development may describe one or more of motor, vision, hearing, speech, comprehension, cognitive, language, and/or other abilities of the user, as inferred from analyzing the monitored activity of the user in the virtual environment. For instance, the motor abilities of the user may be inferred based on input rates and/or reaction times of one or more input devices, such as a mouse and/or keyboard. Further, the hearing abilities of the user may be inferred based on how a user responds to aural stimili such as instructions articulated by an announcer in the virtual environment. Other abilities of the user may be similarly inferred.

In one embodiment, the level of development may be expressed in terms of an inferred age of the user. Because even users of the same age may have varying developmental characteristics, the age being inferred is not necessarily the actual age of the user but is a classification of the user into a predetermined age group. Each age group may be distinctly identified by a respective age or age range. For example, age ranges may include four to six years of inferred age, six to thirteen years of inferred age, etc. Each age range represents users having abilities characteristic of developmentally sound users of the respective age range. Additionally or alternatively, each age group may be distinctly identified by a respective group name. For example, group names may include newborn, infant, toddler, preschooler, child, teenager, adolescent, etc. At least in some embodiments, each group name may be associated with a respective age or age range. For example, "preschooler" may be associated with users between four to six years of inferred age.

As described above, once a profile has been generated for the user, social elements in the virtual environment may be programmatically tailored for the user, based on the profile. Depending on the embodiment, the tailoring may be performed by a virtual world server and/or a virtual world client. As used herein, a social element refers to any aspect of the virtual environment that affects a manner in which a user interacts with other users in the virtual environment. In many virtual environments, such interactions occur via respective avatars belonging to and controlled by each user. Further, each social element may be specific to a user (or avatar). In other words, tailoring a social element for a given user may not necessarily entail tailoring that social element for any other user in the virtual environment. As used herein, tailoring a social element refers to changing the behavior of the social element in a way that is perceptible by the user in the virtual environment.

In one embodiment, social elements may be programmatically tailored to create a more socially engaging and/or fulfilling experience for the user. Further, the user need not necessarily be burdened with the task of manually configuring a vast array of options relating to social elements of the virtual environment. In particular, developmentally young users may not necessarily be able to configure or even comprehend such an array of options. Developmentally young users may include users of a corresponding age and users (of any age) with a developmental disorder such as autism and Asperger's Syndrome. However, in some embodiments, user options may nevertheless be provided to allow at least some users to override decisions programmatically made for those users.

For example, tailoring a social element may include determining which avatars should be in the vicinity of the avatar of the user. Doing so allows the user to more easily interact with other users of similar interests and/or levels of development, as indicated by the activity profiles and development profiles, respectively. The avatar of the user may be spawned at a location in the virtual environment proximate to such other users. The spawning may occur in response to the user entering a virtual world upon login and/or the user explicitly requesting a re-spawn of the avatar. Further, at least in some embodiments, the degree of proximity may be user-configurable, where the degree of proximity is measured in terms of a unit of distance in the virtual environment.

As another example, tailoring a social element may include determining how many avatars should be in the vicinity of the avatar of the user. At least in some embodiments, reducing the number of avatars may also reduce an extent to which the user may feel overwhelmed by the sheer number of avatars (and/or interactions therebetween) proximate to the user in the virtual environment. Interactions between avatars may include textual conversation, voice chat, activities, etc. By reducing the number of avatars, developmentally younger users may more easily follow or comprehend interactions in the virtual world and thus may more likely participate in the interactions. Further, regardless of the level of development of the user, reducing the number of avatars may also reduce an environment is perceived to be "spammy" or distracting to the user. Accordingly, the number of avatars may be tailored to create a more socially engaging and fulfilling experience for the user.

On the other hand, in one embodiment, a more socially engaging and fulfilling experience may also be created by increasing—rather than reducing—the number of avatars in the vicinity of the avatar of the user. Depending on the level of development of the user, the increase in the number of avatars (and the interactions therebetween) may be perceived as creating a more lively social atmosphere for the user.

In one embodiment, tailoring a social element may include determining what types of textual information should be presented to the user. Types of textual information may pertain to avatars in the vicinity of the avatar of the user and may include textual conversation, activities, achievements, emoticons, etc. As with tailoring the number of avatars described above, the types of textual information presented to the user may be tailored to suit the level of development of the user, to create a more socially engaging and fulfilling experience for the user.

In one embodiment, tailoring a social element may include determining a manner in which textual information should be presented to the user. The manner may include a format and/or layout of the textual information. For instance, textual information may be presented in a larger font for a developmentally young user. Further, the layout of the textual information may also be simplified for the developmentally young user. As used herein, the layout of textual information refers to placement, orientation, and associated graphical user interface (GUI) elements for presenting the textual information, as opposed to GUI screens depicting the virtual environment itself.

Although embodiments are described herein with respect to tailoring social elements of the virtual environment, in other embodiments, any element of the virtual environment may be tailored, including non-social elements. For example, developmentally young users may prefer a reduced display resolution and/or an increased avatar size, so that the users may more easily see the avatars in the virtual environment. Other embodiments not departing from the scope of the present disclosure are broadly contemplated.

In one embodiment, tailoring a social element may include determining what types of avatars should be in the vicinity of the user. Types of users may include friends of the user and strangers to the user in the virtual environment. A friend of the user refers to another user whom the user previously indicated to add to a list of friends of the user. Alternatively, types of users may be determined based on number of degrees of friends from the user. For example, friends of the first degree (i.e., the user's friends) is a first user type, and friends of the second degree (i.e., friends of the first degree friends) is a second user type. The types of users may also be determined using other techniques. For example, in a virtual environment accessible to both paying users and non-paying users, the types of users may be determined based on whether the respective user is a paying user.

Although embodiments are described herein with respect to monitoring activity of the user in the virtual environment, any information associated with the user may be used to tailor social elements of the virtual environment. For example, in one embodiment, when monitoring activity of the user, an associated network address of the user may be logged. An example of a network address is an Internet Protocol (IP) address. Geolocation techniques may then be used to approximate a location of the user in the physical world, based on the logged network address or other information such as city, state, country, and/or ZIP supplied by the users. The approximated location may be stored in a geographical profile of the user. By comparing geographical profiles, users who are proximate to the user in the physical world may be identified. Using the techniques described above, the user may be placed proximate to such users in the virtual environment. Doing so may increase a likelihood that the user encounters people whom the user is already acquainted with in the physical world. Doing so may also avoid privacy implications of alternative approaches. One alternative approach includes explicitly indicating that certain users may be acquainted with one another or may be proximate to one another in the physical world.

Further, although embodiments are described herein with respect to determining which avatars should be in the vicinity of the avatar of the user, other embodiments are broadly contemplated. For example, in an alternative embodiment, only the visibility of the avatars as perceived by the user is changed. In other words, the avatars may still be present in the vicinity of the user but are not visible to the user. Further, any textual information associated with the avatars may also be withheld from being presented to the user.

In one embodiment, after tailoring a given social element in the virtual world, the activity of the user may be further monitored to determine if and/or how the given social element should be further tailored. For example, assume that the number of avatars visible to the user is increased from ten avatars to twenty avatars, based on one or more profiles of the user. Assume also that subsequent to the increase, the rate of interaction of the user decreases, such as in terms of frequency of chatting textually, frequency of engaging in activities with other avatars, etc. In response, the virtual world server and/or client may conclude that the number of avatars was increased too greatly and further adjust the number of avatars down to fifteen avatars. At least in some embodiments, the further tailoring of social elements may be selectively enabled by the user.

Further, although embodiments are described herein with respect to a single virtual world, other embodiments are broadly contemplated. For example, in some embodiments, the activity of a user may be monitored across multiple virtual environments. Further, profiles generated for the user may be specific to a given virtual environment or may apply across multiple virtual environments. Further still, social elements tailored for the user may apply to a given virtual environment or may apply across multiple virtual environments.

In one embodiment, to safeguard the privacy of users of the virtual world, data collected from the users and/or activity monitored may be anonymized and/or aggregated based on predetermined user privacy settings. For example, sensitive information of a user such as a full name may be replaced with a numerical identifier for the user. As another example, a city attribute of type string and associated with the user may be removed altogether or replaced with a numerical city identifier, depending on the desired level of privacy. As a further example, an age attribute, whether specified by the user or derived for the user, may be replaced with an age group attribute, where the age group has an age range satisfying the desired level of privacy. Additionally or alternatively, statistical measures may be derived in the aggregate from multiple users rather than from a single user. Depending on the embodiment, the user privacy settings may apply to all users of a virtual world or only to one or more specific users of the virtual world. The user privacy settings may be specified by a developer or administrator of the virtual world and may be tailored to suit the privacy needs of a particular case. At least in some embodiments, users of the virtual world may influence or even override part or all of the user privacy settings. In some embodiments, only users beyond a threshold age (as specified by the user or inferred for the user) may influence or override part or all of the user privacy settings. Doing so provides finer control over the user privacy settings to advanced users while also reducing a likelihood of younger users unintentionally or unwittingly overriding the user privacy settings.

Figure 1:
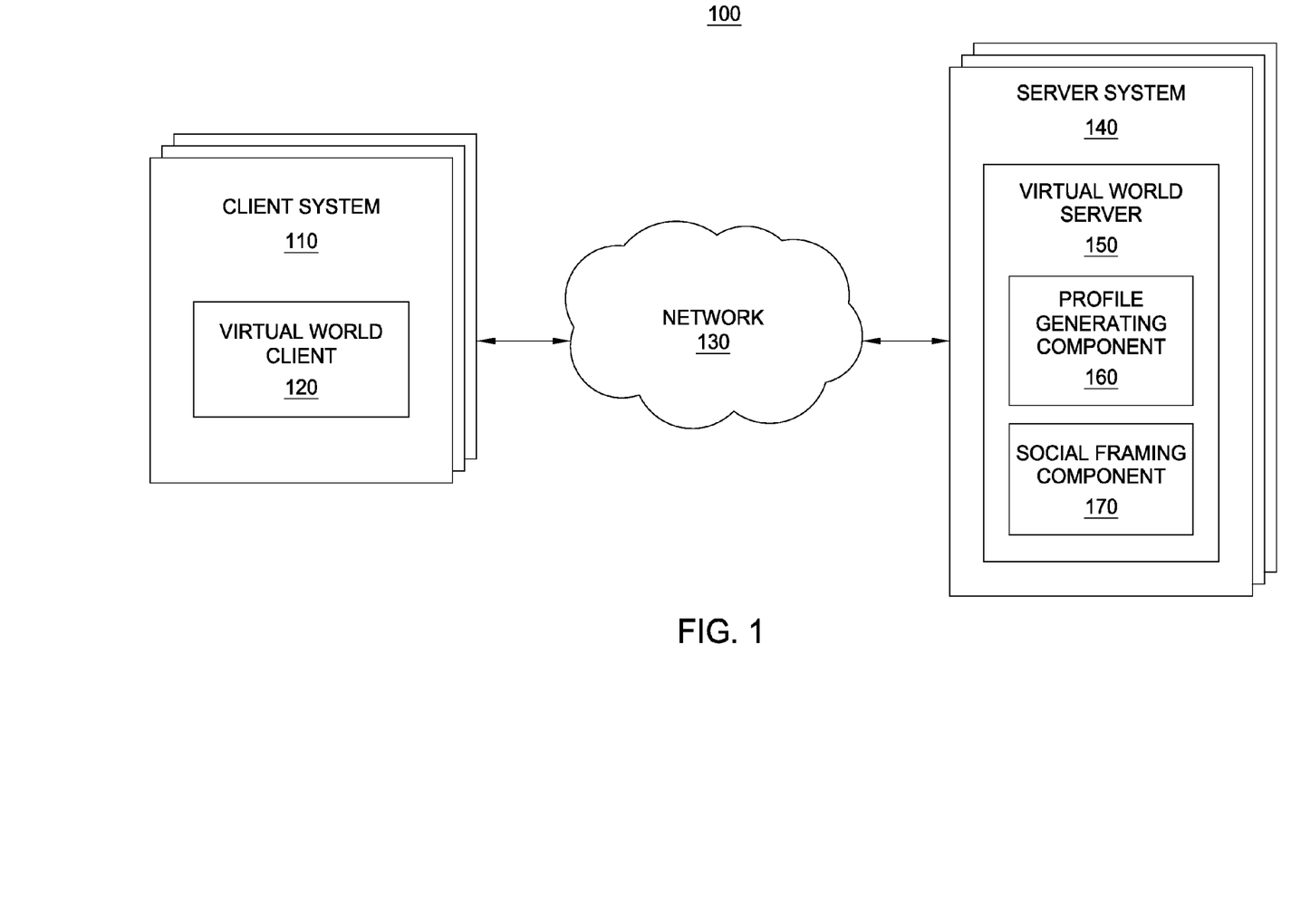
FIG. 1 is a block diagram illustrating a system configured to provide a social platform in a virtual environment, according to one embodiment of the present invention.

FIG. 1 is a block diagram illustrating a system 100 configured to provide a social platform in a virtual environment, according to one embodiment of the present invention. As shown, the system 100 includes a plurality of client systems 110 connected to a plurality of server systems 140 via a network 130. Each of the client systems 110 is configured to operate a virtual world client 120. Examples of the client systems 110 include, without limitation, console gaming systems (e.g., the Microsoft Xbox 360®, the Sony Playstation® 3, etc.), handheld gaming systems (e.g., the Nintendo 3DS™ and DS™, the Sony PSP®, etc.), personal computer gaming systems and so on.

The server systems 140 are configured to operate a virtual world server 150. Generally, the virtual world server 150 is configured to receive connections from users (e.g., via the virtual world clients 120) and to manage a virtual world and interactions between the users within the virtual world. Further, the virtual world server 150 includes a profile generating component 160 and a social framing component 170. Although embodiments are described herein with reference to the virtual world server 150 monitoring user activity in the virtual environment, in other embodiments, an activity monitoring component (not shown) in the virtual world server 150 performs such functions.

In one embodiment, the profile generating component 160 generates one or more profiles of a user, based on monitored activity of the user in the virtual environment. As described above, each profile may be an activity profile or a developmental profile. An activity profile specifies activities in the virtual environment that the user often engages in. For example, suppose that the monitored activity of a user, Bob, indicates that he spends much of his time in the virtual environment on a personal computer (PC) playing a racing game in single-player mode and for ten minutes at a time. From the monitored activity, the profile generating component 160 may create an activity profile such as the one shown in Table I.

TABLE I

Example of Activity Profile for Bob

| User: | Bob |
|---|---|
| Profile Type: | Activity Profile (Inferred) |
| Preferred genres: | Racing |
| Preferred modes: | Single player |
| Preferred play duration: | 10 minutes |
| Preferred device: | PC |

As shown in Table I, the activity profile for Bob indicates that Bob appears to prefer racing games, single-player gaming, PCs, and gaming sessions of approximately ten minutes in duration. The activity profile of Bob may be compared with activity profiles of other users to determine users having interests closely matching the interests of Bob, based on predetermined matching criteria. Such functionality is further described below with reference to the social framing component 170. Further, Bob need not necessarily be burdened with the task of manually specifying preferences relating to activities in the virtual environment. Nevertheless, in some embodiments, Bob may be presented with user options to manually modify and/or override one or more aspects of the activity profile.

As described above, in one embodiment, a developmental profile specifies a level of development of the user in the physical world. For example, suppose that Bob is an eight-year-old child of sound development. Based on the monitored activity of Bob in the virtual environment, the profile generating component 160 may create a development profile such as the one shown in Table II.

TABLE II

Example of Development Profile for Bob

| User: | Bob |
|---|---|
| Profile Type: | Development Profile (Inferred) |
| Criteria: | Motor abilities only |
| Level of development: | 8-10 years old |

As shown in Table II, the development profile of Bob indicates that based solely on the motor abilities of Bob in the virtual environment, Bob is inferred to have a level of development on par with that of soundly-developed eight- to ten-year-olds. For example, the motor abilities of Bob may be evaluated based on how quickly and/or accurately Bob uses a mouse and/or keyboard in response to prescribed stimuli in the virtual environment. In one embodiment, the prescribed stimuli may be presented to Bob as an explicit motor abilities test. In other embodiments, the prescribed stimuli may be part or all of an activity in the virtual environment (such as a racing event), such that Bob is not necessarily aware that his motor abilities are being assessed. Further, the criteria may be tailored to suit the needs of a particular case. Further, Bob need not necessarily be burdened with the confusing and/or frustrating task of manually providing information relating to his level of development. Nevertheless, in some embodiments, Bob may be presented with user options to manually modify and/or override one or more aspects of the development profile.

Figure 2:
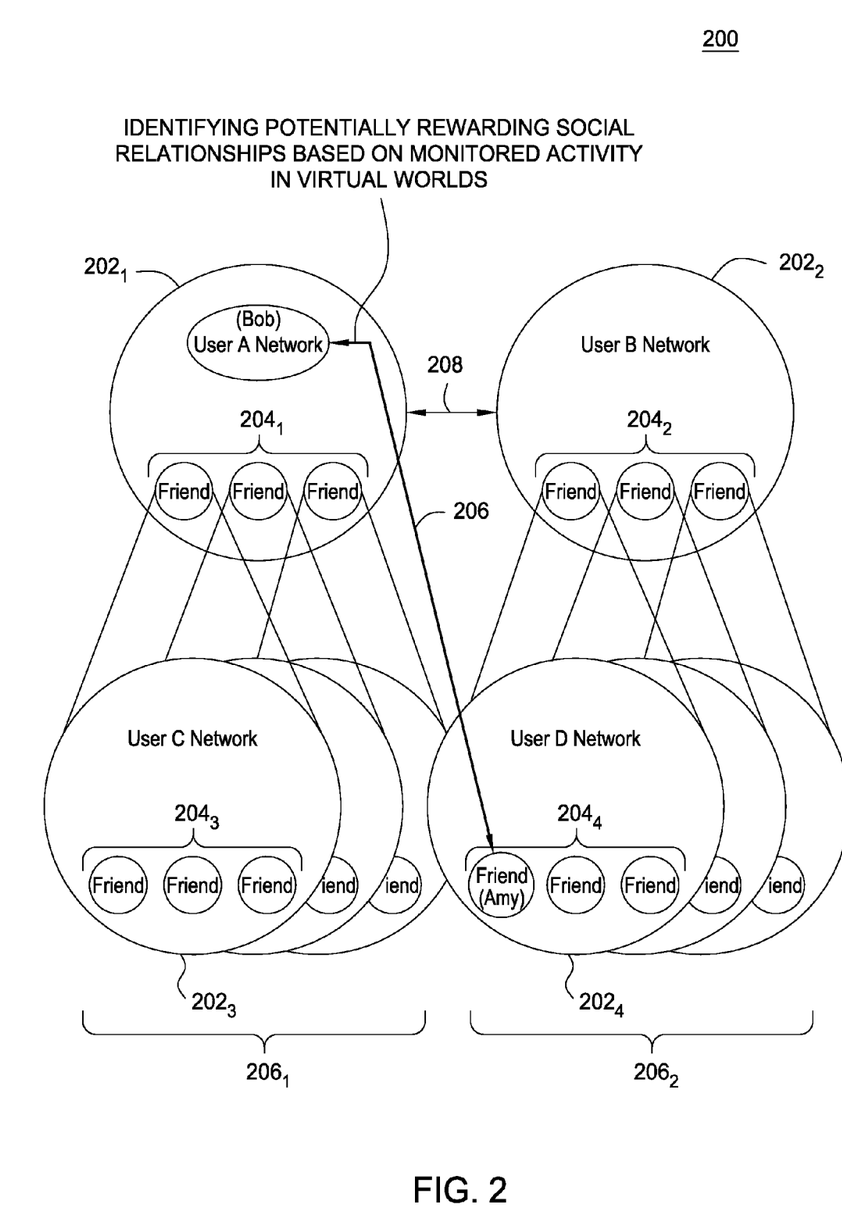
FIG. 2 is a diagram depicting friend networks of two users in the virtual environment, according to one embodiment of the invention.

FIG. 2 is a diagram 200 depicting friend networks of two users in the virtual environment, according to one embodiment of the invention. The two users include users A and B. A first-degree network $202_1$ of user A includes friends $204_1$, and the first-degree network $202_2$ of user B includes friends $204_2$. The friends $204_{1-2}$ may also themselves have first-degree networks $202_{3-4}$ and friends $204_{3-4}$ therein, respectively. Suppose that user B is also a first-degree friend of user A, as indicated by a relationship line 208. The second-degree network of user A includes networks $206_1$ and the network $202_2$. The second-degree network of user B includes the network $202_4$. Similarly, the third-degree network of user A also includes the network $202_4$.

In one embodiment, the social framing component 170 tailors one or more social elements of the virtual world, based on generated profiles. To this end, the social framing component 170 may identify users having similar profiles. Suppose user A is Bob, and suppose that the third-degree network of user A includes a user, Amy. Further, suppose that the profile generating component 160 creates an activity profile for Amy, such as the one shown in Table III.

TABLE III

Example of Activity Profile for Amy

| User: | Amy |
|---|---|
| Profile Type: | Activity Profile (Inferred) |
| Preferred genres: | Racing, Puzzle |
| Preferred modes: | Single player |
| Preferred play duration: | 12 minutes |
| Preferred device: | Handheld |

As shown in Table III, the activity profile for Amy indicates that Amy appears to prefer racing and puzzle games, single-player gaming, handhelds, and gaming sessions of approximately twelve minutes in duration. The social framing component 170 may identify Amy as a sufficiently close match to Bob, based on similarities in preferred genre, mode, and play duration and despite differences in preferred device. The identification is depicted as a line 206 in FIG. 2. Once identified, the virtual world server and/or client may attempt to increase a likelihood of Bob and Amy encountering one another in the virtual environment. For example, the likelihood may be increased using any of the techniques described above, such as spawning the avatar of Bob in the vicinity of the avatar of Amy when Bob logs in.

Further, in some embodiments, each aspect of the activity profile may be assigned a respective, prescribed weight. The weights specify which aspects of an activity profile are more heavily favored during the matching process. For example, if "genre" is discovered to be a strong matching criteria, than "genre" may be assigned a higher weight than "device".

In some embodiments, the matching criteria may also exclude users not within a given number of degrees of friends from a given user. This property of the matching criteria may also be configured and/or overridden by the given user. Further, depending on the embodiment, users may be matched based on a single profile type (e.g., activity profile, developmental profile, or geographical profile) or multiple profile types.

In one embodiment, once the virtual world server 150 detects that Amy and Bob have begun interacting with one another in the virtual environment, the virtual world server 150 may recommend activities to Amy and Bob, based on their respective profiles. For example, the virtual world server 150 may recommend racing activities or other 10-12 minute activities to Amy and/or Bob. In one embodiment, the recommendations may be selectively disabled by a user.

Figure 3:
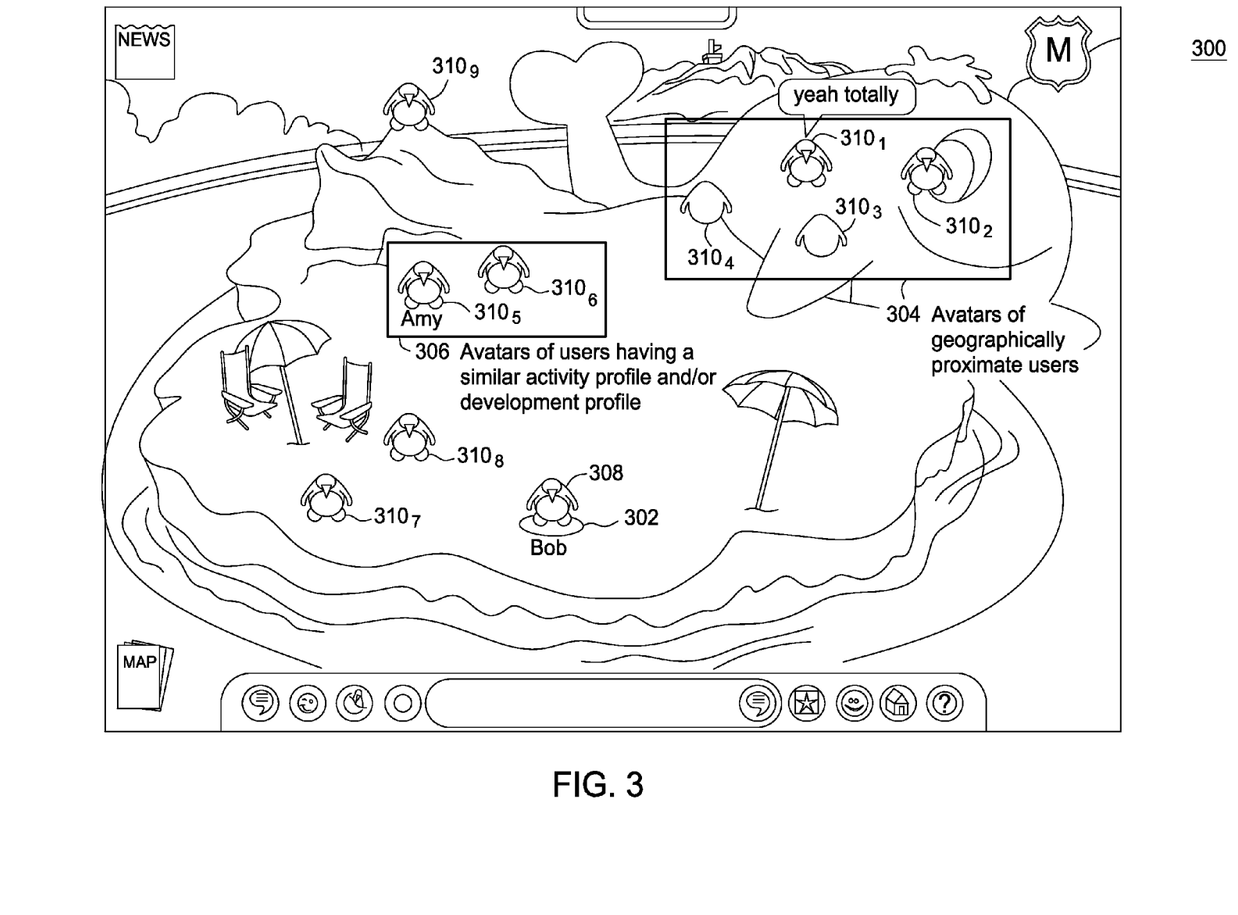
FIG. 3 is a graphical user interface (GUI) screen of the virtual environment as perceived by a user upon logging in, according to one embodiment of the invention.

FIG. 3 is a GUI screen 300 of the virtual environment as perceived by Bob when Bob logs in, according to one embodiment of the invention. The location in the virtual environment at which an avatar is spawned is also referred to as a landing point (or spawn point) of the avatar. As described above, the landing point of the avatar of Bob may be selected to increase a likelihood of Bob having a more socially engaging and/or fulfilling experience in the virtual environment. To this end, the avatar of Bob may be spawned proximate to avatars of users that have a similar activity profile, developmental profile, and/or geographical profile.

As shown, the avatar 308 of Bob is spawned at a landing point 302 that is proximate to other avatars. The other avatars include a first group 306 of avatars of users having a similar activity profile and/or developmental profile as Bob. The other avatars further include a second group 304 of avatars having a similar geographical profile as Bob. The other avatars further include avatars $310_{7-9}$ of three users not known to have any profiles matching those of Bob. Such avatars $310_{7-9}$, when proximate to the avatar of the user, may help maintain a sense of authenticity of the virtual world, to the extent that the user anticipates or appreciates the opportunity to speak with randomly encountered users (who are generally not very likely to have too much in common with the user). The first group 306 includes avatars $310_{5-6}$, and the second group 304 includes avatars $310_{1-4}$. The avatar $310_5$ is the avatar of Amy, who is described above to have at least an activity profile matching that of Bob. Accordingly, by spawning the avatar of Bob at the landing point 302, the likelihood of Bob and Amy encountering one another in the virtual environment may be increased.

Figure 4:
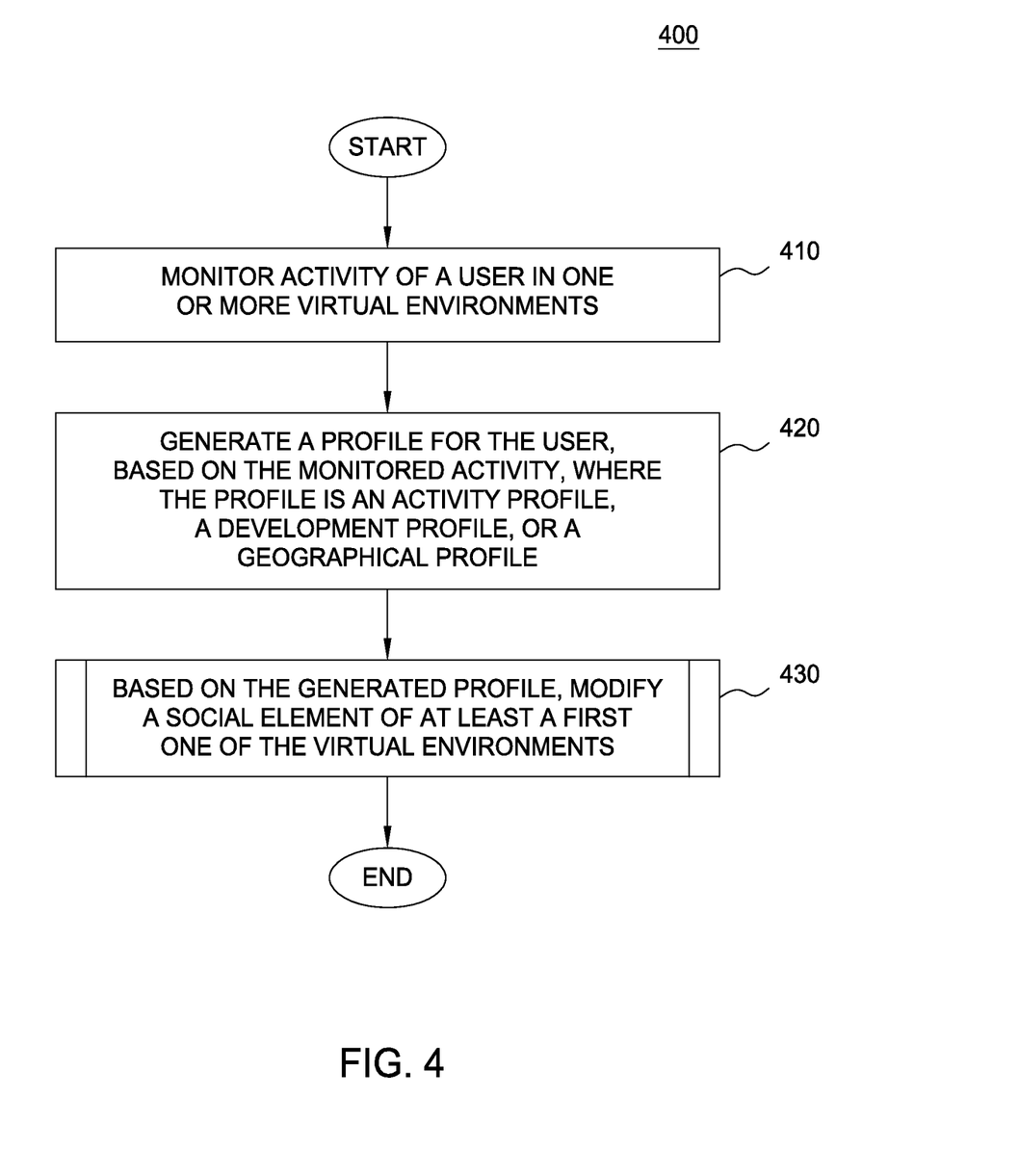
FIG. 4 is a flowchart depicting a method for providing a social platform in a virtual environment, according to one embodiment of the invention.

FIG. 4 is a flowchart depicting a method 400 for providing a social platform in a virtual environment, according to one embodiment of the invention. As shown, the method 400 begins at step 410, where the virtual world server 150 monitors activity of the user in one or more virtual environments. At step 420, the profile generating component 160 creates a profile for the user, based on the monitored activity, where the profile is an activity profile, a developmental profile, or a geographical profile. At step 430, the social framing component 170 modifies a social element of at least a first one of the virtual environments, based on the generated profile. The step 430 is further described below in conjunction with the method 500 of FIG. 5. After the step 430, the method 400 ends.

Figure 5:
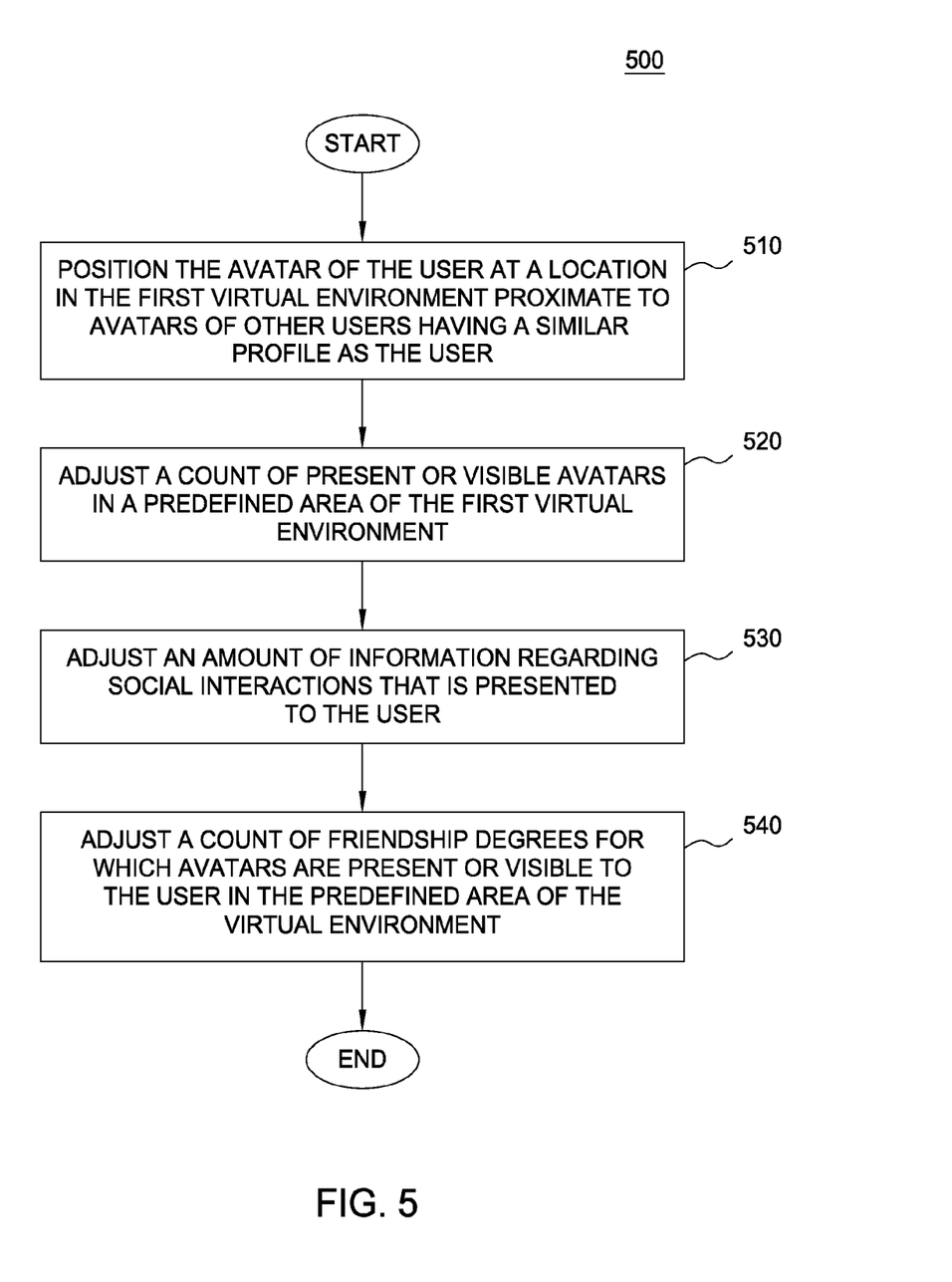
FIG. 5 is a flowchart depicting a method for modifying a social element of a virtual environment, according to one embodiment of the invention.

FIG. 5 is a flowchart depicting a method 500 for modifying a social element of a virtual environment, according to one embodiment of the invention. The method 500 corresponds to the step 430 of FIG. 4 and may include one or more of the following operations. At step 510, the virtual world server 150 positions the avatar of the user at a location in the virtual environment proximate to avatars of other users having a similar profile as the user. At step 520, the virtual world server 150 adjusts a count of present or visible avatars in a predefined area of the first virtual environment. For example, the predefined area may be a virtual room in the virtual environment. At step 530, the virtual world server 150 adjusts an amount of information regarding social interactions that is presented to the user. At step 540, the virtual world server 150 adjusts a count of friendship degrees for which avatars are present or visible to the user in the predefined area of the virtual environment. After the step 540, the method 500 ends.

Figure 6:
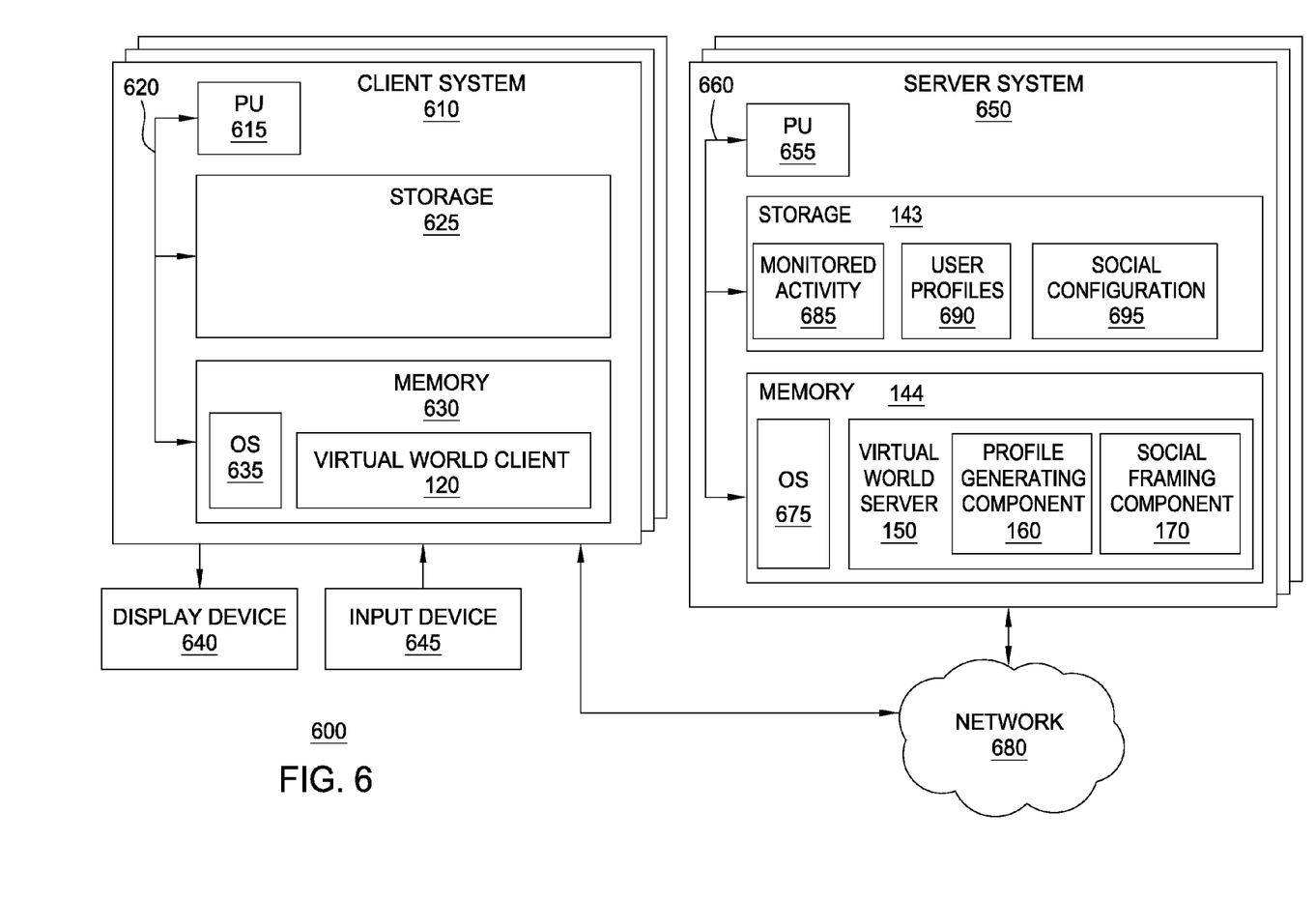
FIG. 6 is a block diagram illustrating a system configured to provide a social platform, according to one embodiment of the invention.

FIG. 6 is a block diagram illustrating a system 600 configured to provide a social platform, according to one embodiment of the invention. As shown, the system 600 includes a plurality of client systems 610 and a server system 650, communicatively coupled via a network 680. In one embodiment, the client systems 610 may include existing computer systems, e.g., desktop computers, server computers, laptop computers, tablet computers, gaming consoles, hand-held gaming devices and the like. The client systems 610 illustrated in FIG. 6, however, are merely examples of computer systems in which embodiments of the present invention may be used. Embodiments of the present invention may be implemented differently, regardless of whether the computer systems are complex multi-user computing systems, such as a cluster of individual computers connected by a high-speed network, single-user workstations, or network appliances lacking non-volatile storage. Moreover, it is explicitly contemplated that embodiments of the invention may be implemented using any device or computer system capable of performing the functions described herein.

As shown, each client system 610 includes, without limitation, a processor 615, which obtains instructions and data via a bus 620 from a memory 630 and storage 625. Processor 615 is a programmable logic device that performs instruction, logic, and mathematical processing, and may be representative of one or more CPUs. Storage 625 is representative of hard-disk drives, flash memory devices, optical media and the like. Generally, the storage 625 stores application programs and data for use by the client system 610. The client systems 610 are operably connected to the network 680, e.g., via network interfaces.

The memory 630 is any memory sufficiently large to hold the necessary programs and data structures. Memory 630 could be one or a combination of memory devices, including Random Access Memory, nonvolatile or backup memory (e.g., programmable or Flash memories, read-only memories, etc.). In addition, memory 630 and storage 625 may be considered to include memory physically located elsewhere; for example, on another computer coupled to the client system 610 via bus 620. The memory 630 includes the virtual world client 120 and an operating system ("OS") 635. Operating system 635 is software used for managing the operation of the client system 610. Examples of OS 635 include UNIX, versions of the Microsoft Windows® operating system and distributions of the Linux® operating system. Additional examples of OS 635 include custom operating systems for gaming consoles, including the custom operating systems for systems such as the Microsoft Xbox 360®, Nintendo WHO and Sony PlayStation® 3.

Additionally, the client systems 610 each are coupled to display devices 640 and input devices 645. The display devices 640 may include output devices such as monitors, touch screen displays, and so on. For instance, the display devices 640 may include a display device used to visually depict a virtual environment. As an example, the display 640 may provide a touch sensitive surface allowing the user to select different locations within the virtual environment and control the movement of an avatar within the virtual environment. The input devices 645 represent a wide variety of input devices, including keyboards, mice, controllers, and so on. Furthermore, the input devices 645 may include a set of buttons, switches or other physical device mechanisms for controlling the client system 610. For example, the input devices 645 could include a set of directional buttons used to navigate an avatar through a virtual environment presented on the display 640.

As shown, the server system 650 includes, without limitation, a processor 655, which obtains instructions and data via a bus 660 from a memory 670 and storage 665. Processor 655 is a programmable logic device that performs instruction, logic, and mathematical processing, and may be representative of one or more CPUs. Storage 665 is representative of hard-disk drives, flash memory devices, optical media and the like. Generally, the storage 665 stores application programs and data for use by the server system 650. The server system 650 is operably connected to the network 680, e.g., via a network interface.

The memory 670 is any memory sufficiently large to hold the necessary programs and data structures. Memory 670 could be one or a combination of memory devices, including Random Access Memory, nonvolatile or backup memory (e.g., programmable or Flash memories, read-only memories, etc.). In addition, memory 670 and storage 665 may be considered to include memory physically located elsewhere; for example, on another computer coupled to the server system 650 via bus 660. The memory 670 includes the virtual world server 150 and an operating system ("OS") 675. Operating system 675 is software used for managing the operation of the server system 650. Examples of OS 675 include UNIX, versions of the Microsoft Windows® operating system and distributions of the Linux® operating system. Additional examples of operating system 675 include custom operating systems for gaming consoles, including the custom operating systems for systems such as the Microsoft Xbox 360®, Nintendo Wii® and Sony PlayStation® 3.

The virtual world server 150, in turn, includes the profile generating component 160 and the social framing component 170. As discussed above, the profile generating component 160 creates profiles for each user, based on the monitored activity of the respective user in the virtual environment. The social framing component 170 tailors one or more social elements of the virtual environment, based on the created profiles. Accordingly, for a given user, the likelihood of encountering other users having similar profiles is increased. As a result, the virtual environment may be more socially engaging to the user.

In the preceding, reference is made to embodiments of the invention. However, the invention is not limited to specific described embodiments. Instead, any combination of the following features and elements, whether related to different embodiments or not, is contemplated to implement and practice the invention. Furthermore, although embodiments of the invention may achieve advantages over other possible solutions and/or over the prior art, whether or not a particular advantage is achieved by a given embodiment is not limiting of the invention. Thus, the preceding aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications (e.g., the virtual world server 150) or related data available in the cloud. For example, the virtual world server 150 could execute on a computing system in the cloud and receive a login request from a user (e.g., from the virtual world client 120 associated with the user). In such a case, the virtual world server 150 could determine a spawn point for the user, proximate to other users having a similar profile as the user. Doing so increases a likelihood that the user would encounter other users having something in common with the user.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. Each block of the block diagrams and/or flowchart illustration, and combinations of blocks in the block diagrams and/or flowchart illustration, can be implemented by special-purpose hardware-based systems that perform the specified functions or acts, or combinations of special purpose hardware and computer instructions.

While the foregoing is directed to embodiments of the present invention, other and further embodiments of the invention may be devised without departing from the basic scope thereof, and the scope thereof is determined by the claims that follow.

What is claimed is:

1. A computer-implemented method of programmatically tailoring social elements of a virtual environment to users, the computer-implemented method comprising:

monitoring activity of a user in the virtual environment, wherein the monitored activity comprises input from the user in response to a stimulus in the virtual environment, wherein the input is provided using an input device for controlling an avatar associated with the user in the virtual environment, wherein the monitored activity is at least one of: (i) anonymized and (ii) aggregated based on a predetermined user privacy setting;

generating, based on analyzing the monitored activity, an activity profile, a developmental profile, and a geographical profile, wherein the activity profile identifies: (i) the user; (ii) a first profile type; (iii) an activity genre preferred by the user; (iv) an activity mode preferred by the user; (v) an activity duration preferred by the user; and (vi) a device type preferred by the user, wherein the development profile identifies: (i) the user; (ii) a second profile type; (iii) a development criteria against which to measure the user; and (iv) a level of development of the user and according to the development criteria, wherein the geographical profile identifies: (i) the user; (ii) a third profile type; (iii) a network address associated with the user, wherein the network address comprises an Internet Protocol (IP) address; and (iv) a geographical location of the user, determined based on the network address using a predefined geolocation technique, and wherein the first, second, and third profile types are distinct profile types;

evaluating motor abilities of the user based on a quickness and an accuracy of the input during the monitored activity;

determining that the user belongs to a subset of a plurality of users of the virtual environment identified as being developmentally young, based on the evaluated motor abilities of the user and irrespective of an actual age of the user, wherein determining that the user belongs to the subset of the plurality of users identified as being developmentally young is based on determining that the user has a developmental disorder;

by operation of one or more computer processors and based on the determination that the user belongs to the subset of users identified as being developmentally young, modifying, specifically for the user, a social element between the user and at least one other user of the virtual environment, without receiving, from the user, any request to modify the social element, wherein at least one other user of the plurality of users does not have any social element so modified, and wherein modifying the social element comprises placing the avatar associated with the user in a location in the virtual environment that is within a predefined distance of a plurality of other users who were also determined to belong to the subset of users identified as being developmentally young, wherein modifying the social element further comprises:

receiving, from the user, either (i) an indication to enter the virtual environment or (ii) an indication to respawn the avatar;

identifying, for the user, a spawn point in the virtual environment, wherein the spawn point is proximate to a threshold count of other users having at least one of a similar activity profile and a similar developmental profile as the user; and positioning the avatar for the user at the identified spawn point;

subsequent to modifying the social element, measuring an extent to which the user is interacting with avatars in the virtual environment; and further modifying the social element in the virtual environment, based on the measured extent and further based on at least one of the activity profile and the developmental profile.

2. The computer-implemented method of claim 1, wherein modifying the social element further comprises adjusting how many avatars are present or visible to the user in a predefined area in the virtual environment.

3. The computer-implemented method of claim 1, wherein modifying the social element further comprises changing how much information regarding social interactions is presented to the user.

4. The computer-implemented method of claim 1, wherein modifying the social element further comprises adjusting a layout in which textual information regarding the virtual environment is presented to the user.

5. The computer-implemented method of claim 1, wherein modifying the social element further comprises adjusting how many relationship degrees for which avatars are present or visible to the user in a predefined area in the virtual environment, and wherein the monitored activity is at least one of anonymized or aggregated based on a predetermined user privacy setting.

6. A non-transitory computer-readable medium containing a program which, when executed, performs an operation to programmatically tailor social elements of a virtual environment to users, the operation comprising:

monitoring activity of a user in the virtual environment, wherein the monitored activity comprises input from the user in response to a stimulus in the virtual environment, wherein the input is provided using an input device for controlling an avatar associated with the user in the virtual environment, wherein the monitored activity is at least one of: (i) anonymized and (ii) aggregated based on a predetermined user privacy setting;

generating, based on analyzing the monitored activity, an activity profile, a developmental profile, and a geographical profile, wherein the activity profile identifies: (i) the user; (ii) a first profile type; (iii) an activity genre preferred by the user; (iv) an activity mode preferred by the user; (v) an activity duration preferred by the user; and (vi) a device type preferred by the user, wherein the development profile identifies: (i) the user; (ii) a second profile type; (iii) a development criteria against which to measure the user; and (iv) a level of development of the user and according to the development criteria, wherein the geographical profile identifies: (i) the user; (ii) a third profile type; (iii) a network address associated with the user, wherein the network address comprises an Internet Protocol (IP) address; and (iv) a geographical location of the user, determined based on the network address using a predefined geolocation technique, and wherein the first, second, and third profile types are distinct profile types;

evaluating motor abilities of the user based on a quickness and an accuracy of the input during the monitored activity;

determining that the user belongs to a subset of a plurality of users of the virtual environment identified as being developmentally young, based on the evaluated motor abilities of the user and irrespective of an actual age of the user, wherein determining that the user belongs to the subset of the plurality of users identified as being developmentally young is based on determining that the user has a developmental disorder;

by operation of one or more computer processors and based on the determination that the user belongs to the subset of users identified as being developmentally young, modifying, specifically for the user, a social element between the user and at least one other user of the virtual environment, without receiving, from the user, any request to modify the social element, wherein at least one other user of the plurality of users does not have any social element so modified, and wherein modifying the social element comprises placing the avatar associated with the user in a location in the virtual environment that is within a predefined distance of a plurality of other users who were also determined to belong to the subset of users identified as being developmentally young, wherein modifying the social element further comprises:

receiving, from the user, either (i) an indication to enter the virtual environment or (ii) an indication to re-spawn the avatar;

identifying, for the user, a spawn point in the virtual environment, wherein the spawn point is proximate to a threshold count of other users having at least one of a similar activity profile and a similar developmental profile as the user; and positioning the avatar for the user at the identified spawn point;

subsequent to modifying the social element, measuring an extent to which the user is interacting with avatars in the virtual environment; and further modifying the social element in the virtual environment, based on the measured extent and further based on at least one of the activity profile and the developmental profile.

7. The non-transitory computer-readable medium of claim 6, wherein modifying the social element further comprises adjusting how many avatars are present or visible to the user in a predefined area in the virtual environment.

8. The non-transitory computer-readable medium of claim 6, wherein modifying the social element further comprises changing how much information regarding social interactions is presented to the user.

9. The non-transitory computer-readable medium of claim 6, wherein modifying the social element further comprises adjusting a layout in which textual information regarding the virtual environment is presented to the user.

10. The non-transitory computer-readable medium of claim 6, wherein modifying the social element further comprises adjusting how many relationship degrees for which avatars are present or visible to the user in a predefined area in the virtual environment, and wherein the monitored activity is at least one of anonymized or aggregated based on a predetermined user privacy setting.

11. A system to programmatically tailor social elements of a virtual environment to users, the system comprising:

one or more computer processors; and a memory containing a program which, when executed by the one or more computer processors, is configured to perform an operation comprising:

monitoring activity of a user in the virtual environment, wherein the monitored activity comprises input from the user in response to a stimulus in the virtual environment, wherein the input is provided using an input device for controlling an avatar associated with the user in the virtual environment, wherein the monitored activity is at least one of: (i) anonymized and (ii) aggregated based on a predetermined user privacy setting;

generating, based on analyzing the monitored activity, an activity profile, a developmental profile, and a geographical profile, wherein the activity profile identifies: (i) the user; (ii) a first profile type; (iii) an activity genre preferred by the user; (iv) an activity mode preferred by the user; (v) an activity duration preferred by the user; and (vi) a device type preferred by the user, wherein the development profile identifies: (i) the user; (ii) a second profile type; (iii) a development criteria against which to measure the user; and (iv) a level of development of the user and according to the development criteria, wherein the geographical profile identifies: (i) the user; (ii) a third profile type; (iii) a network address associated with the user, wherein the network address comprises an Internet Protocol (IP) address; and (iv) a geographical location of the user, determined based on the network address using a predefined geolocation technique, and wherein the first, second, and third profile types are distinct profile types;

evaluating motor abilities of the user based on a quickness and an accuracy of the input during the monitored activity;

determining that the user belongs to a subset of a plurality of users of the virtual environment identified as being developmentally young, based on the evaluated motor abilities of the user and irrespective of an actual age of the user, wherein determining that the user belongs to the subset of the plurality of users identified as being developmentally young is based on determining that the user has a developmental disorder;

based on the determination that the user belongs to a subset of users identified as being developmentally young, modifying, specifically for the user, a social element between the user and at least one other user of the virtual environment, without receiving, from the user, any request to modify the social element, wherein at least one other user of the plurality of users does not have any social element so modified, and wherein modifying the social element comprises placing the avatar associated with the user in a location in the virtual environment that is within a predefined distance of a plurality of other users who were also determined to belong to the subset of users identified as being developmentally young, wherein modifying the social element further comprises:

receiving, from the user, either (i) an indication to enter the virtual environment or (ii) an indication to re-spawn the avatar;

identifying, for the user, a spawn point in the virtual environment, wherein the spawn point is proximate to a threshold count of other users having at least one of a similar activity profile and a similar developmental profile as the user; and positioning the avatar for the user at the identified spawn point;

subsequent to modifying the social element, measuring an extent to which the user is interacting with avatars in the virtual environment; and further modifying the social element in the virtual environment, based on the measured extent and further based on at least one of the activity profile and the developmental profile.

12. The system of claim 11, wherein modifying the social element further comprises adjusting how many avatars are present or visible to the user in a predefined area in the virtual environment.

13. The system of claim 11, wherein modifying the social element further comprises adjusting how much information regarding social interactions is presented to the user.

14. The system of claim 11, wherein modifying the social element further comprises adjusting a layout in which textual information regarding the virtual environment is presented to the user.

15. The computer-implemented method of claim 1, wherein the social element comprises at least one of:

(i) a first social element specifying how many avatars are present or visible to the user in a predefined area in the virtual environment and which social element, when lowered, reduces the level of complexity associated with engaging in social activities in the virtual environment;

(ii) a second social element specifying how much information regarding social interactions is presented to the user and which social element, when lowered, reduces the level of complexity associated with engaging in social activities in the virtual environment;

(iii) a third social element specifying a layout in which information regarding the virtual environment is presented to the user and which social element, when simplified, reduces the level of complexity associated with engaging in social activities in the virtual environment; and (iv) a fourth social element specifying how many relationship degrees for which avatars are present or visible to the user in a predefined area in the virtual environment and which social element, when lowered, reduces the level of complexity associated with engaging in social activities in the virtual environments.

16. The method of claim 1, wherein the subset of the plurality of users of the virtual environment identified as being developmentally young further includes the at least one other user, wherein the at least one other user has a corresponding young age, but does not have a developmental disorder.

17. The non-transitory computer-readable medium of claim 6, wherein the subset of the plurality of users of the virtual environment identified as being developmentally young further includes the at least one other user, wherein the at least one other user has a corresponding young age, but does not have a developmental disorder.

* * * * *